(12) United States Patent  (10) Patent No.: US 9,179,868 B2
Yu et al.  (45) Date of Patent: Nov. 10, 2015

(54) FINGERSTALL OXIMETER

(75) Inventors: Wenbing Yu, Beijing (CN); Jiuhe Jin, Beijing (CN); Wei Wang, Beijing (CN); Changbo Li, Beijing (CN)

(73) Assignee: Beijing Choice Electronic Technology Co., Ltd., Beijing (CN)

( * ) Notice: Subject to any disclaimer, the term of this patent is extended or adjusted under 35 U.S.C. 154(b) by 422 days.

(21) Appl. No.: 13/514,427

(22) PCT Filed: Dec. 23, 2010

(86) PCT No.: PCT/CN2010/080177
§ 371 (c)(1),
(2), (4) Date: Jun. 7, 2012

(87) PCT Pub. No.: WO2012/083543
PCT Pub. Date: Jun. 28, 2012

(65) Prior Publication Data
US 2012/0323096 A1  Dec. 20, 2012

(51) Int. Cl.
*A61B 5/1455* (2006.01)
*A61B 5/00* (2006.01)

(52) U.S. Cl.
CPC ......... *A61B 5/14551* (2013.01); *A61B 5/14552* (2013.01); *A61B 5/6826* (2013.01)

(58) Field of Classification Search
CPC .................................................... A61B 5/1455
USPC ................................................. 600/310–344
See application file for complete search history.

(56) References Cited

U.S. PATENT DOCUMENTS

| | | | |
|---|---|---|---|
| 6,014,576 A * | 1/2000 | Raley | 600/344 |
| 6,654,621 B2 * | 11/2003 | Palatnik et al. | 600/322 |
| 7,742,794 B2 | 6/2010 | Todokoro et al. | |
| 2010/0198028 A1 | 8/2010 | Wang | |

FOREIGN PATENT DOCUMENTS

| | | |
|---|---|---|
| CN | 201098122 Y | 8/2008 |
| CN | 101411618 A | 4/2009 |
| CN | 201333039 Y | 10/2009 |
| CN | 201585988 U | 9/2010 |
| WO | 2009114963 A1 | 9/2009 |

* cited by examiner

*Primary Examiner* — Eric Winakur
*Assistant Examiner* — Marjan Fardanesh
(74) *Attorney, Agent, or Firm* — The Webb Law Firm

(57) ABSTRACT

Disclosed is a fingerstall oximeter including a soft gum coat and a case, a display screen for displaying measurement results is provided on the upper part of the case and an open corresponding to the display screen is provided on the soft gum coat. The soft gum coat is slipped over the outside of the case, the case is used to accommodate and protect a circuit board, and a chamber for accommodating finger is formed and rounded by the upper part of the case and the bottom of the soft gum coat, for accommodating a finger to be measured. A first measurement module is provided on the bottom of the soft gum coat and a second measurement module is provided within the case at a position corresponding to the first measurement module.

8 Claims, 2 Drawing Sheets

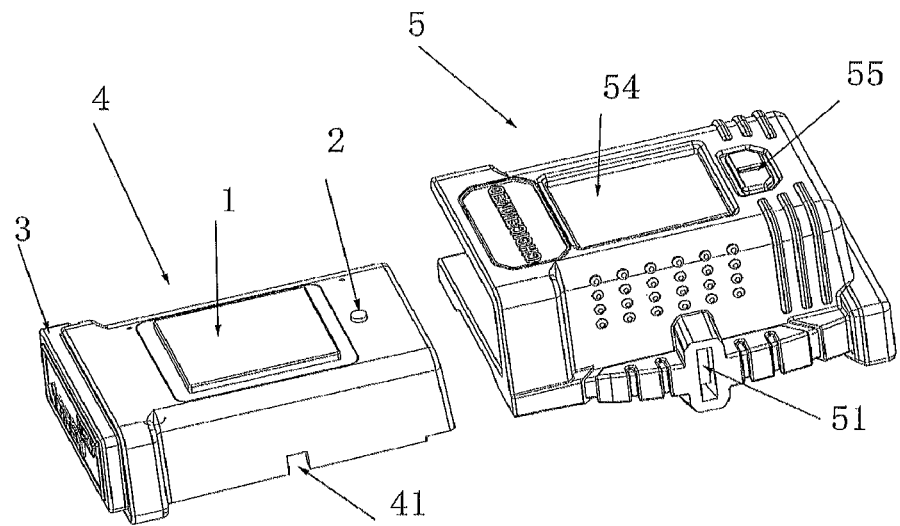
Fig.1a      Fig.1b
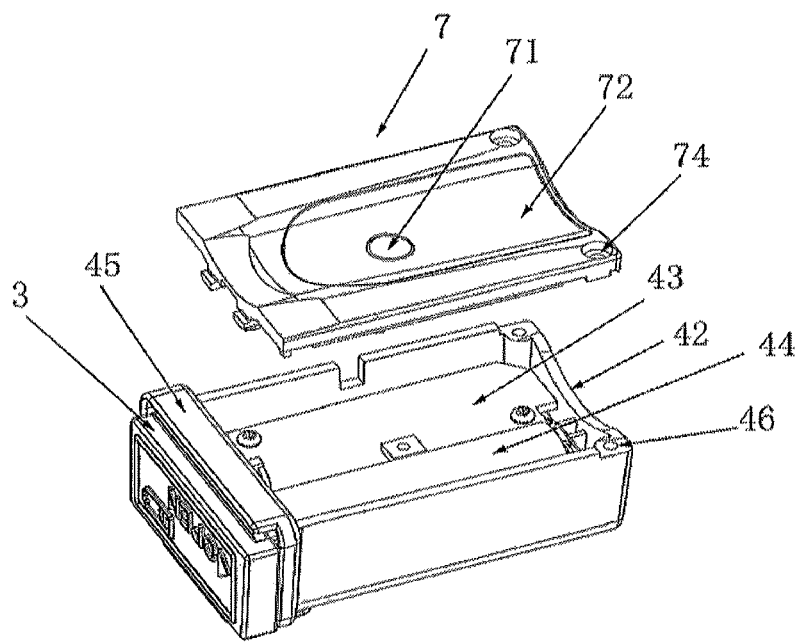
Fig.2

FINGERSTALL OXIMETER

FIELD OF THE INVENTION

The present invention relates to a technical field of medical equipment, and particularly relates to a fingerstall oximeter.

BACKGROUND OF THE INVENTION

With the development of the socioeconomy and the improvement of the living standard, people pay more attention to their health care, and more and more families begin measuring pulse rate and degree of blood oxygen saturation using some home testing apparatus, in particular some patients with respiratory diseases and cardiovascular disease. For example, more and more families have a favor in an oximeter. Current oximeters are generally classified into two kinds, i.e. finger-clipped oximeters and fingerstall oximeters, and the fingerstall oximeter is favored since it can provide better finger comfort and higher accuracy.

An existing fingerstall oximeter includes a soft gum coat and a case. A measurement element is provided on the soft gum coat, other circuit elements for processing data and displaying are provided within the case, and a chamber for accommodating finger is formed by the case and the soft gum coat. The measurer only needs to place his finger in the chamber for accommodating finger so as to obtain the pulse rate and the degree of blood oxygen saturation, so the fingerstall oximeter has advantages of simple measurement operations, small volume, easy to carry, and monitoring the pulse rate and the degree of the blood oxygen saturation at any moment etc.

For example, a Chinese Patent Application No. 200920246562.9 discloses such a fingerstall oximeter. The fingerstall oximeter includes a soft gum coat and a case, the soft gum coat and the case are formed integrally of same material to be a big cavity, and a finger stop plate is provided in the big cavity to divide it into two chambers, one is used for accommodating measurement elements and data processing elements, and the other is used for accommodating the finger to be measured, wherein a metal fender is embedded in the upper part of the soft gum coat for mounting and protecting the elements. Such an oximeter is not robust since there is only one metal fender used as a mounting bracket, and the assemblage is more complex since parts of the oximeter need to be mounted in the integrally formed big cavity respectively. In addition, the fingerstall oximeter has a small battery compartment which may only accommodate batteries of small electrical quantity and small size, thereby shortening the usage time, and it is not convenient for the user (especially old people) to replace the batteries since the large force combining the battery cover and the oximeter.

SUMMARY OF THE INVENTION

The object of the present invention is to solve the problems mentioned above and provides a fingerstall oximeter which can be easily assembled and is more robust, while is small in volume and is longer in usage time.

To this end, the present invention provides a fingerstall oximeter, which includes a soft gum coat and a case, a display screen is provided on the upper part of the case to display a measurement result, an open corresponding to the display screen is provided on the soft gum coat, the soft gum coat is slipped over the outside of the coat, the coat is used for accommodating and protecting the circuit boards, a chamber for accommodating finger is formed and surrounded by the lower part of the case and the bottom of the soft gum coat to accommodate a finger to be measured, a first measurement module is provided on the bottom of the soft gum coat and a second measurement module is provided in the case at a position corresponding to the first measurement module. The circuit boards are integrated with a data processing module, a power management module, a data collecting module and a data communication interface.

The case includes a circuit board chamber and a battery chamber which are juxtaposed, the battery chamber is used for accommodating a dry cell, and the circuit board chamber is used for accommodating the circuit boards; only one dry cell can be accommodated in the battery chamber for supplying power to the fingerstall oximeter.

A finger stop plate is provided in the lower part of the case, and the finger stop plate and the bottom of the soft gum coat surround and form the chamber for accommodating finger; preferably, the finger stop plate is formed to be an arc, and the front side of the case is formed to be an arch-shaped edge corresponding to the arc; preferably, a soft gum pad is provided on the finger stop plate.

The finger stop plate and the case are combined with each other by means of a buckle and a screw, or the finger stop plate and the case are formed integrally.

A flange is provided on the upper part of the end of the case, a roundabout part adapting the flange is provided on the soft gum case, the roundabout part and the soft gum coat form a trench into which the flange can be embedded, so that the case and the soft gum coat can be fitted closely.

A battery cover is provided on the back side of the case, and the battery cover is connected to the case via a pivot and is buckled up with the case in a sliding manner.

The case is made from metal materials or hard organic materials, wherein a corresponding insulating layer is required when the metal materials is used, so as to insulate the case from the circuit elements within the case.

Using the fingerstall oximeter provided by the present invention, the following advantageous effects can be achieved.

In the fingerstall oximeter of the present invention, since a case for accommodating circuit elements is provided independently, most of the circuit elements are provided in the case, so that circuit elements can be protected better and can not be damaged easily, while such an arrangement can also make it easy to assemble the oximeter and make it more robust. When circuit elements are assembled into the case, the remaining assemble procedure is only to make the circuit elements within the case electrically connect to the measurement element on the bottom of the soft gum coat and slip the soft gum coat over the case, so the assemblage of the oximeter of the present invention is made to be easier, and the soft gum coat can reduce the damage to the case and the circuit elements in the case due to the drop and other collision, which make the oximeter more robust. In addition, the soft gum coat and the case are combined by slipping the soft gum coat over the case, which make it easier to replace and clean the soft gum coat, and maintain or replace circuit elements.

In addition, in a preferred embodiment of the present invention, the case is divided into two juxtaposed chambers, i.e. a battery chamber and a circuit board chamber, which makes the thickness of the case smaller compared with the situation in which two cases are provided up and down or other similar situations; moreover, the battery chamber is provided to be a chamber for one cell, reducing the width of the case, thereby a case with smaller thickness and smaller width can be used. So, in the fingerstall oximeter of the present invention, space of the case is fully used and the overall volume is reduced.

BRIEF DESCRIPTION OF THE DRAWINGS

FIG. 1a is an overall structural view of a case of the fingerstall oximeter of the present invention;

FIG. 1b is a schematic structural view of a soft gum coat of the fingerstall oximeter of the present invention;

FIG. 2 is a detailed structural view of the case of the fingerstall oximeter of the present invention;

DETAILED DESCRIPTION OF THE PREFERRED EMBODIMENTS

Figure 3:
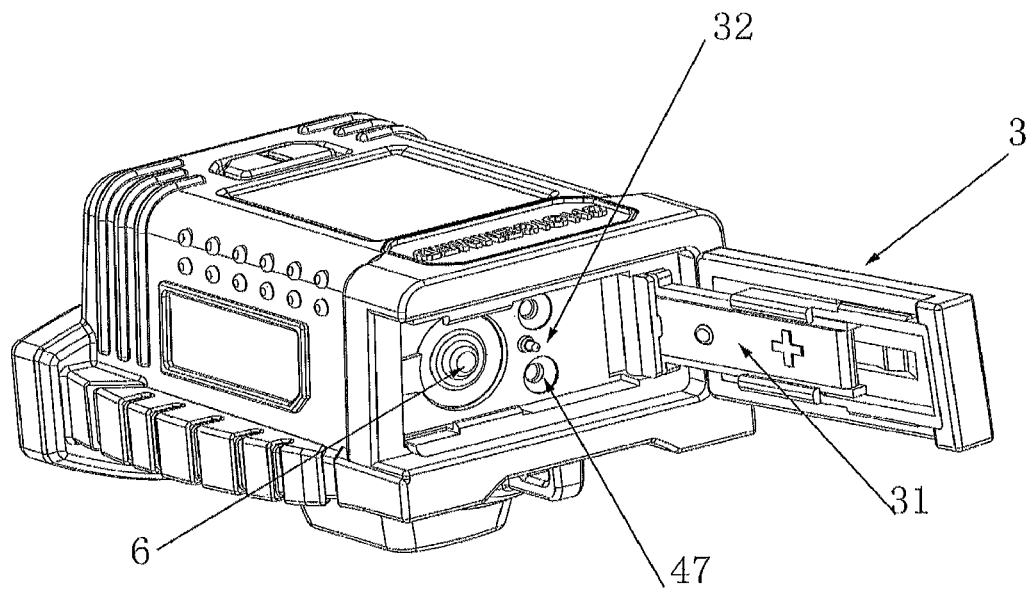
FIG. 3 is a schematic structural view of a batteries cover of the fingerstall oximeter of the present invention.

In order to provide a better understanding of the technical solutions of the present invention for the persons skilled in the art, the fingerstall oximeter provided by the present invention will be described in detail below in combination with the figures.

For the purpose of easy description, it is assumed that the front side or the front end cited in the present invention refers to a side closer to the aperture of the chamber for accommodating finger of the soft gum coat, and the back side or the end cited in the present invention refers to a side beyond the aperture of the chamber for accommodating finger of the soft gum coat; the upper part or the upper end cited in the present invention refers to a side the display screen locates, and the lower part, the bottom or the lower side cited in the present invention refers to a side opposite to the display screen.

Referring to FIGS. 1a to 4 all together, the fingerstall oximeter provided by the present invention includes a soft gum coat 5, a case 4, a battery 6 and a data processing module, a power management module, a data collecting module and a data communicating interface within the case 4 or the soft gum coat 5.

An open is provided on the back side of the soft gum coat 5, through which the soft gum coat 5 can be slipped over the case 4. A chamber for accommodating finger 8 is formed and surrounded by the upper part of the case 4 and the bottom of the soft gum coat 5, and is used for accommodating the finger to be measured. The open is positioned above the chamber for accommodating finger 8, so that the open will not run through the chamber for accommodating finger 8. A first measurement module in the data collecting module is mounted on the bottom of the soft gum coat 5, a second measurement module in the data collecting module is provided on the case 4 at a position corresponding to the first measurement module, and each of the first and second measurement modules is one of an emission circuit board and a reception circuit board, that is, one of the first and second measurement modules is the emission circuit board for emitting measurement light beams and the other is the reception circuit board for receiving measurement light beams passing through the finger to be measured and transmitting the measurement data to the data processing module, the measurement data is processed so as to obtain the oxygen content of blood in the human body. The case 4 is made from metal materials or hard organic materials (a corresponding insulating layer required when the metal materials is used, so as to insulate the case from the circuit boards within the case), has higher hardness and strength, and can protect the circuit elements disposed in the case 4 effectively.

The soft gum coat 5 has a higher physical tenderness and flexibleness and can attach on the case 4 closely, and the soft gum coat bottom 53 surrounding the chamber for accommodating finger 8 can vary with the finger profile and wrap around the finger closely, while a higher usage comfort can be achieved.

Specific structures of the case 4 and the soft gum coat 5 will be described below in detail in combination of the Figures.

As shown in FIGS. 1a and 1b, a display screen 1 and a button 2 are provided on the upper part of the case 4. An open 54, which adapts the display screen 1 in shape, and a button protection part 55, which adapts the button 2 in shape and is hollow, are provided on the upper part of the soft gum coat 5. In order to facilitate communication between the circuit boards in the case 4 and the circuit boards on the bottom of the soft gum coat 5, a notch 41 is provided on a side face of the case 4, while a wiring duct 51 is provided on the soft gum coat 5 at a position corresponding to the notch 41, so that corresponding wires are easily assembled, neat, and not disorder.

In practical applications, the circuit boards on the bottom of the soft gum coat 5 and the soft gum coat 5 may be formed integrally and corresponding connecting wires may be led out through the wiring duct 51 and a wiring hole provided on the soft gum coat 5. Thus, when the fingerstall oximeter provided by the present invention is assembled, the circuit boards in the case 4 may be mounted first, then the led-out connecting wires are connected to the circuit boards in the case 4 through the notch 41, and finally the soft gum coat 5 is slipped over the case 4, thereby simplifying the assemblage procedure greatly.

As shown in FIG. 2, a partition board is provided inside the case 4 to divide the inside of the case 4 into two juxtaposed chambers, i.e. a circuit board chamber 43 and a battery chamber 44. The circuit board chamber 43 is used to accommodate the data processing circuit board, and the data processing circuit board is integrated with the data processing module, the power management module, the data collecting module and the data communication interface; the battery chamber 44 is used to accommodate the battery 6 which supplies power to the circuit boards of the oximeter. A finger stop plate 7 is provided in the lower part of the case 4, and the chamber for accommodating finger 8 is formed and surrounded by the finger stop plate 7 and the bottom 53 of the soft gum coat to accommodate the finger to be measured. In order to increase comfort, the finger stop plate 7 is shaped to be an arc and is pasted with a soft gum pad 72, while the front side of the case 4 is formed with an arc edge so as to adapt the finger stop plate 7. A transparent window 71 is provided on the finger stop plate 7 at a position corresponding to the second measurement module, so as to pass the light beams. The finger stop plate 7 and the case 4 can be combined by means of a buckle, and also can be combined by means of a screw. In this embodiment, the finger stop plate 7 and the case is combined by means of a screw, a screwed hole 46 is provided on the front end of the case 4 and a mounting hole 74 is correspondingly provided on the finger stop plate 7. Of course, the finger stop plate 7 and the case 4 can also be formed integrally.

As shown in FIG. 3, a battery cover 3 is arranged on the back side of the case 4, and an electrode slice 31 is arranged on the battery cover 3. The circuit connections are as follows: the positive terminal of the battery is connected to an electrical interface 32 through the electrode slice 31, and is then connected to the data circuit boards etc. The battery cover 3 includes a connecting part and a sliding part, the connecting part is connected to the case 4 via a pivot, and the sliding part can slide at the connecting part and can be buckled up with the case 4, so the battery cover 3 can be opened easily while the force for combining the battery cover 3 with the case is larger.

In addition, two screwed holes for mounting circuit boards may be provided on the back side of the case 4. The battery cover of the present invention is provided on the back side of the case and the way of sliding and buckling is employed, so a battery cover with smaller volume can be used, so as to reduce the volume of the oximeter effectively.

Figure 4:
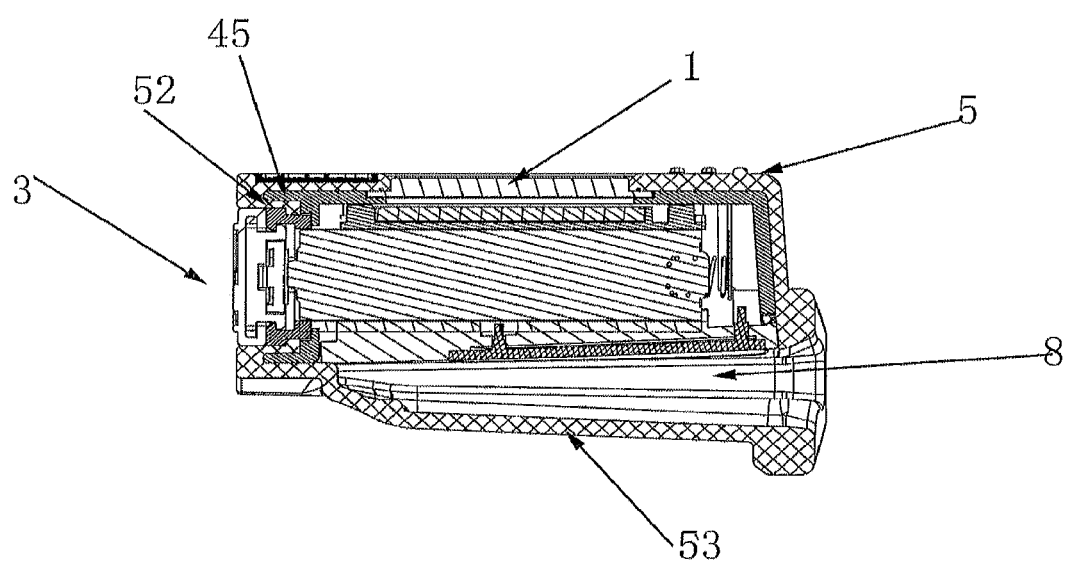
FIG. 4 is a cross-sectional view of the fingerstall oximeter of the present invention.

As shown in FIGS. 2 and 4, in order to make the case 4 and the soft gum coat 5 combined closely, a flange 45 is provided on the case 4 and a roundabout part 52 adapting the flange 45 is provided on the soft gum coat 5. The flange 45 is a part extending outwards of the edge on the back side of the case 4, wherein no flange is provided on the edge of the side the battery cover 3 slides; the roundabout part 52 is a part extending inwards of the end of the soft gum coat 5 and forms a trench with the end of the soft gum coat 5. When the soft gum coat 5 is assembled with the case 4, the flange 4 is embedded in the trench, so as to increase the force combining the case 4 with the soft gum coat 5 and prevent the case 4 slide out of the soft gum coat 5.

The oximeter of the present invention uses the space in the case 4 fully due to the fact that the case is divided into two juxtaposed chambers, and only one dry cell is accommodated in the battery chamber and the space for one dry cell is saved, thereby a case with a smaller volume can be used. In addition, circuit elements including the circuit boards and the battery are all placed within the case 4, so that the fingerstall oximeter of the present invention can be assembled easily and the volume thereof is smaller.

It should be understood that the embodiments mentioned above are exemplary embodiments used to describe the inventive principle. However, the present invention is not limited thereto. It is obvious to those skilled in the art, various modifications and improvements can be made without departing from the spirit and substance of the present invention, all the modifications and improvements are considered to be within the scope of the invention.

What is claimed is:

1. A fingerstall oximeter comprising:
   a soft gum coat,
   a case, which includes a circuit board chamber and a battery chamber, the circuit board chamber and the battery chamber being juxtaposed and separated by a partition,
   a display screen provided on an upper part of the case to display a measurement result, wherein an opening is provided on the soft gum coat at a position corresponding to the display screen, the soft gum coat slipped over the outside of the case, wherein the circuit board chamber of the case accommodates and protects the circuit boards and the battery chamber of the case accommodates a dry cell, and a chamber for accommodating finger is formed and surrounded by a lower part of the case and the bottom of the soft gum coat to accommodate a finger to be measured,
   a first measurement module provided on the bottom of the soft gum coat,
   a second measurement module provided in the case at a position corresponding to the first measurement module, and
   a finger stop plate is provided in the lower part of the case, wherein the chamber for accommodating finger is surrounded by the finger stop plate and the bottom of the soft gum coat.

2. The fingerstall oximeter of claim 1, wherein only one dry cell can be accommodated in the battery chamber for supplying power to the fingerstall oximeter.

3. The fingerstall oximeter of claim 1, wherein the finger stop plate is shaped to be an arc, and the front side of the case is formed to be an arc-shaped edge corresponding to the arc.

4. The fingerstall oximeter of claim 1, further comprising a soft gum pad provided on the finger stop plate.

5. The fingerstall oximeter of claim 1, wherein the finger stop plate is combined with the case by means of a buckle or a screw, or the finger stop plate and the case are formed integrally.

6. The fingerstall oximeter of claim 1, further comprising a flange provided on the upper part of the end of the case, a roundabout part adapting the flange provided on the soft gum coat, wherein the roundabout part and the soft gum coat form a trench into which the flange can be embedded, so that the case and the soft gum coat can be assembled closely.

7. The fingerstall oximeter of claim 1, wherein a battery cover is provided on the back side of the case, and the battery cover is connected to the case via a pivot and can be buckled up with the case in a sliding manner.

8. The fingerstall oximeter of any one of claims 1, 2 and 3 to 7, wherein the case is made from metal materials or hard organic materials.

\* \* \* \* \*